United States Patent [19]

Schoonover et al.

[11] Patent Number: 4,557,899
[45] Date of Patent: Dec. 10, 1985

[54] WATER-IN-OIL TESTING APPARATUS

[75] Inventors: David J. Schoonover; Tillman F. Taylor, Jr., both of Loveland, Colo.

[73] Assignee: Hach Company, Loveland, Colo.

[21] Appl. No.: 660,784

[22] Filed: Oct. 15, 1984

[51] Int. Cl.⁴ .................. G01N 33/18; G01N 33/22
[52] U.S. Cl. ................................ 422/55; 422/58; 422/61; 422/102; 436/40
[58] Field of Search ............... 422/55, 58, 59, 61, 422/68, 102; 436/40, 39, 148

[56] References Cited

U.S. PATENT DOCUMENTS

| | | | |
|---|---|---|---|
| 3,019,342 | 1/1962 | Brooke | 436/40 |
| 3,528,775 | 9/1970 | O'Hara et al. | 436/40 |
| 3,833,340 | 8/1974 | Jones et al. | 436/39 |
| 3,873,271 | 3/1975 | Young et al. | 436/40 |
| 3,973,912 | 8/1976 | Trafton et al. | 422/68 |
| 3,973,915 | 8/1976 | Raffaele et al. | 422/68 |
| 3,976,572 | 8/1976 | Reick | 210/94 |
| 4,089,652 | 5/1978 | Pedersen | 436/40 |
| 4,151,256 | 4/1979 | Pedersen | 436/40 |

*Primary Examiner*—S. Leon Bashore
*Assistant Examiner*—K. M. Hastings
*Attorney, Agent, or Firm*—Dean P. Edmundson

[57] ABSTRACT

Apparatus is described which is useful for determining the water content of a petroleum product. The apparatus includes a reaction vial disposed within a tubular member containing a fluid. As the petroleum product reacts with a reactant in the vial a gas is produced in proportion to the amount of water present in the sample. The gas displaces a liquid from the tubular member, and the amount of liquid displaced is proportional to the amount of water which was present in the petroleum sample.

17 Claims, 3 Drawing Figures

WATER-IN-OIL TESTING APPARATUS

FIELD OF THE INVENTION

This invention relates to detecting the presence of water in oil. More particularly, this invention relates to apparatus and technique for detecting and measuring water present in oil and petroleum products.

CROSS-REFERENCE TO RELATED APPLICATION

Water-in-oil testing methods are described in assignee's copending application Ser. No. 06/660,785, filed Oct. 15, 1984.

BACKGROUND OF THE INVENTION

There are many instances where it is necessary or desirable to determine whether an organic fluid contains water as a contaminant. Oftentimes it is also important to determine the actual amount of water present in such organic medium. For example, it may be necessary to determine the amount of water present in fuels (e.g., diesel fuel, aviation fuel, or gasoline) or in lubricants (e.g., oils).

There have previously been proposed a variety of techniques and apparatus for determining the amount of water contained in an organic medium. Such prior techniques have associated disadvantages and limitations.

In U.S. Pat. No. 3,019,342 there is described a technique for detecting trace amounts of water (e.g., parts per million) in hydrocarbon gas, vapor or light liquids. The hydrocarbon to be tested is contacted with a carbide compound capable of releasing a gas such as acetylene. A preferred carbide is said to be calcium carbide which has been tagged with carbon 14. Then the acetylene-containing effluent is passed through a beta-radiation detector which is calibrated to indicate the amount of moisture in the sample. Alternatively, the amount of acetylene produced can be measured volumetrically. When the tagged calcium carbide is used it may be present in a fluidized bed and nitrogen gas may be used to purge the acetylene gas.

U.S. Pat. No. 3,528,775 describes another technique for determining small amounts of moisture contained in petroleum products. The technique involves collecting a small sample of oil to be tested, then extracting it with methanol in a sealed container, separating the methanol phase, and then titrating it to a visual end point with Karl Fischer reagent.

U.S. Pat. No. 3,833,340 describes another technique for determining water content of liquid mixtures. A material (e.g., concentrated sulfuric acid) which interacts with water to generate a measurable exotherm is added to the mixture being tested, after which the resulting temperature increase is measured. The temperature increase must then be compared with a known relationship between temperature increase and water content.

U.S. Pat. No. 3,873,271 describes a method for detecting undissolved water in hydrocarbons. The method involves exposing a sample of hydrocarbon to freshly ground fuchsia dye and calcium carbonate having an average particle size of less than 10 microns and a surface area of 5-8 square meters per gram. If the sample contains more than 10 parts per million water the dye produces a visually perceptible color.

U.S. Pat. No. 3,976,572 describes a device for indicating the presence of water and other contaminants in aircraft fuel. The device is a transparent cylinder which is divided into upper and lower chambers by means of a filter which permits fuel to pass through it but blocks the flow of water and other contaminants.

U.S. Pat. No. 4,089,652 describes a method for detecting water in oil, wherein the oil sample is brought into contact with a reagent which is reactive with water to produce a gas, in a quantity of inert liquid (e.g., kerosine) which is miscible with the oil sample. The inert liquid is also used as the manometric fluid. As the gas is produced the vessel containing all of the ingredients is maintained in a sealed condition and pressure is allowed to build up. Then after the reaction is completed the inert fluid is allowed to escape from the vessel to an ambient pressure vessel where the volume of displaced inert liquid is measured. This technique requires that the inert liquid (i.e., kerosine) be free of water in order to obtain accurate results. Also, since the gas builds up high pressure, some amount of the gas may be lost through small leaks in the cap. After the test is completed the entire quantity of inert fluid is discarded and the vessel must be thoroughly cleaned and dried before further use.

In U.S. Pat. No. 4,151,256 there is described other apparatus for conducting a detection of water in oil. The apparatus includes a container with associated sample cup for oil to be tested. A collector vessel is attached to the container and a delivery tube is provided leading from the bottom of the container to the collection vessel. A valve is present in the delivery tube so that the interior of the container is completely sealed. A liquid such as petroleum hydrocarbon liquid (e.g, kerosine) which is miscible with the test oil is placed in the container. The reagent (i.e., the ingredient which causes gas to be produced when contacted with water) is then added to the liquid while the cover is off the container. A sample of oil to be tested is then placed in the sample cup which in turn is inserted into the container. The cap is then put on the container tightly. The valve in the delivery tube is also closed tightly. Then the apparatus is tilted and shaken so that the oil sample is mixed thoroughly with the inert liquid. Then the container is allowed to sit until the reaction is complete. Finally, the valve is opened and the pressure of any gas produced will drive the inert liquid out of the container through the delivery tube into the collector where it is measured. This apparatus must be very tightly sealed to be able to completely retain all of the gas produced, which creates a great pressure. After the test the entire contents must be disposed of, and the entire apparatus must be thoroughly cleaned and dried before further use.

SUMMARY OF THE INVENTION

In accordance with the present invention there is provided apparatus for determining the water content of a petroleum product (e.g., an oil). The apparatus provides testing which is simple, accurate and reliable over a broad range of water concentrations. The apparatus is compact and light-weight. The testing may be conducted simply and rapidly without dangerous chemicals or offensive odors. The disadvantages of titrations, color changes, etc. are avoided. Also, messy and time-consuming clean-up of the apparatus is avoided.

The apparatus of the invention comprises:

(a) an outer upright tubular member;

(b) an inner upright tubular member having an outside diameter smaller than the inside diameter of said outer tubular member such that a cavity is defined between said inner and outer tubular members;

(c) sealing means adapted to form a seal between the lower ends of said inner and outer tubular members;

(d) a cap member which is adapted to enclose the top end of the inner and outer tubular members;

(e) a lift tube disposed in the inner tubular member, the lift tube including an opening in its lower portion, and the upper portion of the lift tube is adapted to communicate with the cavity between the inner and outer tubular members;

(f) a reaction vial adapted to contain a sample of said petroleum product to be tested, the vial being disposed within the inner tubular member; and (g) means for introducing the sample into the vial.

The method of the invention involves filling the inner tubular member with ordinary water (e.g., tap water, distilled water, etc.) to a determined level. Then the sample of the petroleum product to be tested is placed in the reaction vial containing a reactant which generates or produces a gas (e.g., hydrogen) when in contact with water in the sample being tested. The resulting gas pressure forces water from the inner tube into the lift tube (and then into the cavity between the inner and outer tanks if the gas produced exceeds the volume of the lift tube).

The amount of water displaced in this manner is proportional to the volume of gas produced and is therefore proportional to the water content in the sample. After the test is complete the reaction vial is either disposed of or cleaned and re-used, as desired. The sample being tested does not leave the reaction vial. Accordingly, it is not necessary to clean the interior of the apparatus after each test. The water which is present in the apparatus may be re-used since it is not contaminated during the testing of the petroleum sample. The apparatus does not require a power supply. Because the lift tube includes graduated marks along its length it serves as a sensitive scale for measuring small amounts of displaced water. The graduated scale along the cavity measures larger quantities of displaced water.

BRIEF DESCRIPTION OF THE DRAWINGS

The invention is described in more detail hereinafter with reference to the accompanying drawings, wherein like reference characters refer to the same parts throughout the several views and in which.

DETAILED DESCRIPTION OF THE INVENTION

Figure 1:
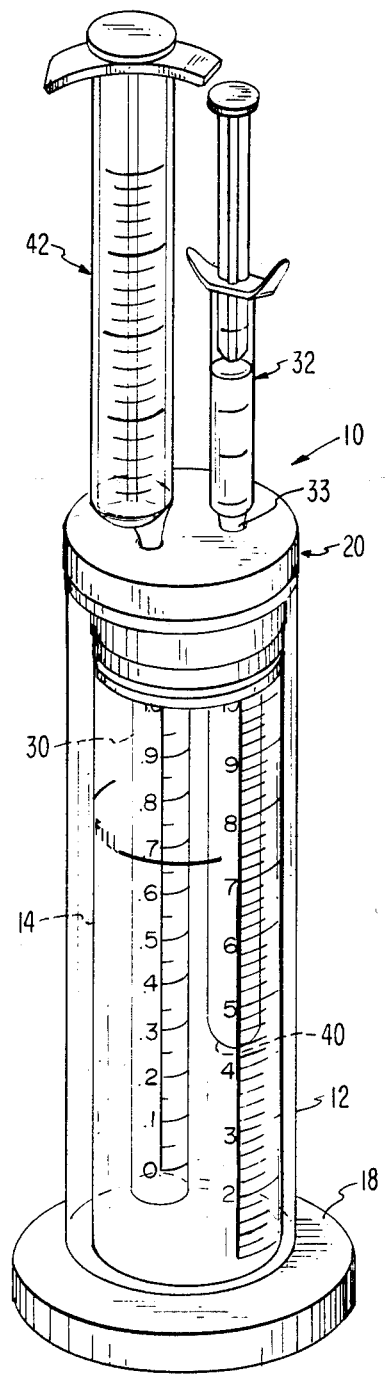
FIG. 1 is a perspective view of one embodiment of testing apparatus of this invention.
Figure 2:
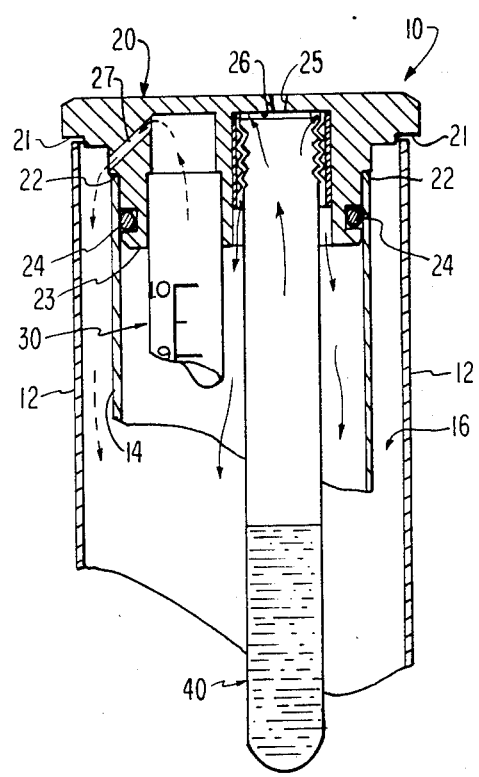
FIG. 2 is a cut-away view of the upper portion of the apparatus of FIG. 1.

In FIGS. 1 and 2 there is shown one embodiment of testing apparatus 10 of this invention. The apparatus includes outer tubular member 12 and inner tubular member 14 whose lower ends are secured to and supported by base member 18. Both of the tubular members are supported in an upright manner and are preferably concentric cylinders (i.e., cylinders having a common axis), as shown. If desired, however, the tubular members may have other shapes (e.g., they may be square, rectangular, oval, polygonal, etc. in cross-section). If desired the tubular members may have non-common axes.

Preferably the tubular members are transparent so that it is possible to see through them. Alternatively, they could be transparent in part and either translucent or opaque in other part.

The tubular members may be made of glass, if desired, although it is more preferably for them to be composed of impact-resistant plastic. For example, a convenient tubing may be made of butyrate, available from Eastman. Other types of useful plastics include acrylic, polycarbonate, polystyrene, polyvinylchloride, and others known in the art.

Between the inner and outer tubular members there is a cavity 16. The lower end of the cavity is conveniently sealed by means of base member 18, although it may be sealed in other manners if desired. When the inner and outer tubular members are cylindrical and co-axial, then the cavity 16 has an annular cross-sectional configuration.

The upper ends of the inner and outer tubular members are enclosed by means of cap member 20. In FIG. 2 there is shown a cross-section of a preferred type of cap member which includes an outer annular shoulder 21, an inner annular shoulder 22, and a central depending portion 23. A rubber or elastomeric O-ring seal 24 is carried by central portion 23 and it is adapted to seal the top of inner tubular member 14, as shown. The inner shoulder 22 is adapted to rest upon the top edge of tubular member 14. The outer shoulder 21 is not adapted to rest upon the top edge of outer tubular member 12; rather, preferably there is a spacing of several thousandths of an inch between shoulder 21 and the outer tube so that air may pass into or out of the cavity 16.

The underside of cap member 20 is also adapted to support lift tube 30 and reaction vial 40. The top end of lift tube 30 may be securely press-fitted into a bore or opening in the underside of the cap member. The top end of the reaction vial may be conveniently threaded into an appropriately threaded bore in the underside of the cap member.

Since it is desired for any gas produced in reaction vial 40 to pass into the inner tubular member 14, there is preferably a space 26 at the top of vial 40 to permit the gas to escape from the vial. A pathway must also be provided back along the threaded portion to enable the gas to enter into the interior of inner tubular member 14. This may be provided by means of vertical slots through the threads in the bore in the cap member, for example. The path of the gas upwardly in vial 40 and downwardly around the outside of vial 40 into tubular member 14 is shown by means of solid arrows in FIG. 2. The pathway is preferably sufficiently large to pass 12.5 milliliters of hydrogen gas per minute, yet it is preferably sufficiently small or convoluted so that water vapor will not diffuse therethrough into the reaction vial before the start of the test.

Opening or aperture 25 in the top of cap member 20 is positioned directly above vial 40 so as to enable a sample to be tested to be injected through the cap member into the vial. For example, the sample may be contained in a syringe 32, and the nose 33 of the syringe may be fitted tightly into aperture 25.

At the top of lift tube 30 there is a passageway 27 which extends through cap member 20 and communicates between lift tube 30 and cavity 16 between inner tube 14 and outer tube 12. Thus, as the water or fluid in inner tube 14 is forced up through lift tube 30 during the test, the volume of displaced water or fluid which exceeds the capacity of the lift tube will pass through passageway 27 and into the cavity 16. Appropriate graduated markings are provided on the lift tube and on the inner tube to indicate the volume of water displaced into the lift tube (or into the cavity if the volume exceeds the capacity of the lift tube). Alternatively, graduated markings may be provided on the outer tube to provide an indication of the amount of water or fluid displaced into the cavity.

Figure 3:
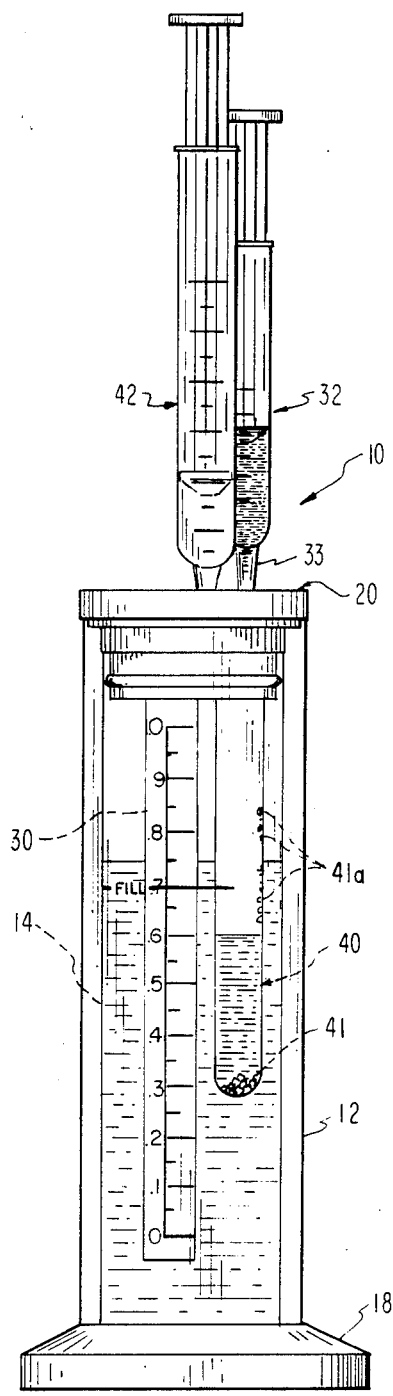
FIG. 3 is side elevational view of the apparatus of FIG. 1.

In FIG. 3 there is shown a side elevational view of the apparatus of FIG. 1 in which the inner tubular member 14 contains ordinary tap water. Initially water was added to tube 14 to the Fill mark and then syringe 42 was used to withdraw sufficient air out of tube 14 so that the water level is even with the bottom of the lift tube 30. This occurs because a slight vacuum is created in tube 14 above the water when air is removed therefrom. Atmospheric pressure then pushes water in lift tube 30 downwardly. When the water level in the lift tube has reached the lower end of the lift tube no more air is removed from tube 14. Alternatively, a small amount of water may be removed from the tube 14 in order to create the slight vacuum.

When 1.0 milliliter of oil sample is then injected into the reaction vial 40 the water level in the lift tube will rise to the zero mark. Then as gas is produced in the reaction vial by reason of water in the oil sample reacting with the reactant therein, the gas will enter the space in inner tube 14 above the water level and force water up the lift tube. If the volume of gas produced exceeds the volume of the lift tube to hold displaced water then the excess water will pass into cavity 16 through passageway 27, as previously explained.

If desired, fluids other than water may be used as the displacement fluid. However, it has been found that ordinary water is the most economical, is readily available, and is the safest fluid for this purpose since it is non-toxic and non-flammable and it may be disposed of without any special precautions. Water does not chemically attack the apparatus.

The apparatus of this invention is very safe in operation because the pressure of the gas produced is not allowed to build up to a high level. Rather, as gas is produced in the reaction vial it passes into the inner tube 14 and displaces water into the lift tube, even if the pressure is very small. Accordingly, the walls of the apparatus may be thin, with no danger of rupture.

The reactant which is used in the reaction vial to produce gas in reaction with water may be a number of different materials. For example, suitable reactants include calcium carbide, calcium hydride, other metal hydrides (e.g., lithium hydride), and reactive metals such as sodium or potassium. The reaction with water in the petroleum sample is a substitution reaction whereby hydrogen gas is produced.

Preferably the reactant is in powdered or granulated form so that there is a large surface area of reactant. It is also preferred for the reactant to be contained in a fluid which is miscible with the petroleum product so that any water present in the sample will be easily released or separated and therefore be available to contact the reactant in the vial. It is also preferred for the fluid to have low vapor pressure at room temperature and low specific gravity (so that the reactant and the water sink to the bottom of the vial). Preferred fluids for this purpose include iso-octane and other inert hydrocarbon fluids of similar boiling point.

If the petroleum product to be tested is a low viscosity liquid such as kerosine, gasoline, aircraft fuel, or the like, it is not necessary to add a fluid such as iso-octane to the reaction vial. Rather the low viscosity petroleum product may be added directly to the reactant. When testing normal viscosity oils it is preferred to add to the reaction vial about 4 milliliters of the fluid such as iso-octane.

The amount of reactant 41 present in the reaction vial 40 should be sufficient to react with all the water present in the petroleum product sample. Typically, when 1 milliliter of petroleum product is being tested the amount of reactant used is 0.3 gram. Preferably the reactant is in powdered or granulated form and is mixed thoroughly with the fluid (e.g., iso-octane) in the reaction vial. Then, while the reaction vial is tipped horizontally, the reactant is permitted to settle from the fluid. In this manner some of the reactant 41A remains adhered to the sides of the reaction vial when the vial is placed in upright position and secured to the cap member. This serves beneficial purposes when the petroleum product is later added to the reaction vial. If there is detergent present in the petroleum product being tested (e.g., motor oil) there is a tendency for the contents of the reaction vial to foam during the reaction. As the foam contacts some of the reactants along the sides or walls of the vial the reactant will react with water in the foam and cause the bubbles to break, thereby releasing the hydrogen gas. At the same time additional fresh reactant is washed down the walls of the vial into the reaction mixture. This increases the reaction rate. Also, since the reaction is exothermic, the heat generated during the reaction speeds the reaction along. When using the apparatus of the invention the reaction typically is complete within two minutes.

The apparatus of this invention may be constructed in various sizes. For example, the height of the tubular members may vary and the diameter may also vary. In general it is preferred for the syringe 32 to be able to hold one milliliter of sample of the petroleum product being tested.

In one embodiment the outer tubular member 12 has an inside diameter of about 2.12 inches and the inner tubular member 14 has an outer diameter of about 1.72 inch, leaving an annular cavity between tubes 12 and 14. The height of the outer tube is 6.75 inches. The lift tube has an inside diameter of about 0.43 inch, and the bottom of the lift tube is about 0.5 inch above the base member 18. The inside diameter of the reaction vial 40 is about 0.5 inch and the capacity of the reaction vial is approximately 11 milliliters. With apparatus of this size it is very convenient to test a 1 milliliter sample of petroleum product containing up to 10% water. If the petroleum product contains more than 10% water a smaller sample of the petroleum product will be used (e.g., 0.5 milliliter). The reading will then be multiplied (e.g., by 2) to obtain the proper percentage reading for water content.

The apparatus just described, which is also illustrated in the drawings, is adapted to conveniently measure water content up to 10%, when using a 1 milliliter sample. Small amounts of moisture content can be read off the graduated scale on the lift tube. Larger amounts of moisture content are read off the scale on tube 14 which indicates the amount of fluid displaced from the interior of tube 14 into cavity 16. With appropriate graduated scales on the lift tube and the tube 14 it is possible to read the percentage of moisture content in the petroleum sample directly off the scale after the test is complete by observing the amount of water or other fluid displaced from tube 14.

The apparatus may be constructed in other sizes, if desired. The particular size described herein is very useful and convenient for most applications. It can be easily packaged, for example, in a kit for convenient shipping or transport. Because it includes two scales (one for sensitive measurement of low percentages of moisture content and one for larger percentages) it provides very accurate results over broad ranges of moisture content in petroleum products.

Other variants are possible without departing from the scope of the present invention.

What is claimed is:

1. Apparatus for determining the water content of a petroleum product comprising:
   (a) an outer upright tubular member;
   (b) an inner upright tubular member having an outside diameter smaller than the inside diameter of said outer tubular member such that a cavity is defined between said inner and outer tubular members;
   (c) sealing means forming a seal between the lower ends of said inner and outer tubular members;
   (d) a cap member which encloses the top end of each of said inner and outer tubular members;
   (e) a lift tube disposed in said inner tubular member, wherein said lift tube includes an opening in its lower portion, and wherein the upper portion of said lift tube communicates with said cavity;
   (f) a reaction vial containing a sample of said petroleum product to be tested and a reactant which produces a gas upon reaction with water; wherein said vial is disposed within said inner tubular member;
   (g) means for introducing said sample of said petroleum product into said vial.

2. Apparatus in accordance with claim 1, wherein said inner and outer tubular members are cylindrical.

3. Apparatus in accordance with claim 2, wherein said inner and outer tubular members are concentric.

4. Apparatus in accordance with claim 1, wherein said sealing means comprises a base member to which the lower ends of said inner and outer tubular members are secured.

5. Apparatus in accordance with claim 1, wherein said reaction vial is suspended from the underside of said cap member.

6. Apparatus in accordance with claim 5, wherein said reaction vial is threadably connected to said cap member in a manner such that gas produced in said reaction vial is permitted to pass into said inner tubular member.

7. Apparatus in accordance with claim 1, wherein the upper end of said lift tube is secured to said cap member, and wherein the lower end of said lift tube is open.

8. Apparatus in accordance with claim 1, wherein said means for introducing said sample into said vial comprises a syringe whose discharge end extends through an aperture in said cap member.

9. Apparatus in accordance with claim 1, wherein said lift tube includes graduated markings along its length.

10. Apparatus in accordance with claim 1, further comprising graduated markings adapted to indicate the level of fluid in said cavity.

11. Apparatus for determining the water content of a petroleum product comprising:
   (a) a base member;
   (b) an outer upright tubular member whose lower end is supported by said base member;
   (c) an inner upright tubular member whose lower end is supported by said base member, wherein said inner tubular member has an outside diameter smaller than the inside diameter of said outer tubular member such that a cavity is defined between said inner and outer tubular members;
   (d) a cap member which encloses the top end of each of said inner and outer tubular members;
   (e) a lift tube suspending from the underside of said cap member, within said inner tubular member, wherein the lower end of said lift tube is open and communicates with the interior of said inner tubular member;
   (f) a passageway communicating between the upper end of said lift tube and said cavity;
   (g) a reaction vial containing a predetermined amount of said petroleum product to be tested and a reactant which produces a gas upon reaction with water, wherein said vial is disposed within said inner tubular member;
   (h) means for introducing said sample of said petroleum product into said vial.

12. Apparatus in accordance with claim 11, wherein said inner and outer tubular members are concentric cylindrical tubes.

13. Apparatus in accordance with claim 11, wherein said reaction vial is adapted to be suspended from the underside of said cap member.

14. Apparatus in accordance with claim 13, wherein said reaction vial is threadably connected to said cap member in a manner such that gas produced in said reaction vial is permitted to pass into said inner tubular member.

15. Apparatus in accordance with claim 11, wherein said means for introducing said sample into said vial comprises a syringe whose discharge end extends through an aperture in said cap member.

16. Apparatus in accordance with claim 11, wherein said lift tube includes graduated markings along its length.

17. Apparatus in accordance with claim 11, wherein said passageway extends through said cap member.

* * * * *